(12) United States Patent
Bauer et al.

(10) Patent No.: US 8,043,582 B2
(45) Date of Patent: Oct. 25, 2011

(54) DOSING DEVICE FOR DOSING A FLUID INTO A RECEIVING CHANNEL OF A TEST ELEMENT FOR ANALYZING BODILY FLUIDS AND METHOD THEREOF

(75) Inventors: Andreas Bauer, Hirschberg (DE); Volker Degenhardt, Heppenheim (DE); Björn Degenhardt, legal representative, Heppenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/556,216

(22) Filed: Sep. 9, 2009

(65) Prior Publication Data
US 2010/0151586 A1    Jun. 17, 2010

(30) Foreign Application Priority Data
Sep. 10, 2008   (EP) .................................... 08015977

(51) Int. Cl.
*B01L 3/02* (2006.01)
(52) U.S. Cl. ......... 422/509; 422/500; 422/501; 422/502
(58) Field of Classification Search ............... 73/864.01, 73/864.13, 864.16, 864.24, 864.25; 506/34, 506/36, 37, 40
See application file for complete search history.

(56) References Cited

U.S. PATENT DOCUMENTS

| | | | |
|---|---|---|---|
| 6,921,514 B1 | 7/2005 | Vetter et al. | |
| 2001/0019845 A1* | 9/2001 | Bienert et al. | 436/181 |
| 2005/0003458 A1* | 1/2005 | Moore et al. | 435/7.2 |
| 2005/0035156 A1 | 2/2005 | Hersch et al. | |
| 2007/0003447 A1* | 1/2007 | Gleason et al. | 422/100 |
| 2007/0272710 A1 | 11/2007 | Bui | |
| 2009/0137062 A1* | 5/2009 | Degenhardt | 436/180 |

FOREIGN PATENT DOCUMENTS

| | | |
|---|---|---|
| EP | 1895308 A1 | 5/2008 |
| WO | 02089982 A2 | 11/2002 |

* cited by examiner

*Primary Examiner* — Yelena G Gakh
*Assistant Examiner* — Christopher A Hixson
(74) *Attorney, Agent, or Firm* — Dinsmore & Shohl, LLP

(57) ABSTRACT

Methods for dosing a fluid into a receiving channel of a test element using a dosing device are disclosed. The dosing device comprises a dosing chamber in fluid connection with a dosing tube having a dosing tip, an optional dosing element extending at least partially into the dosing chamber, a dosing control device, and a movement device for moving the dosing tube and the test element closer to one another. The movement device is actuated to move the dosing tube relative to the test element. The dosing control device is actuated to discharge a fluid into the receiving channel. During the discharge, a fluid bridge forms between the dosing tip and the receiving channel. At the end of the discharge, at least some of the fluid reaches the receiving channel through suction force. A disposable cartridge may be used for dosing a fluid into such a receiving channel.

12 Claims, 8 Drawing Sheets

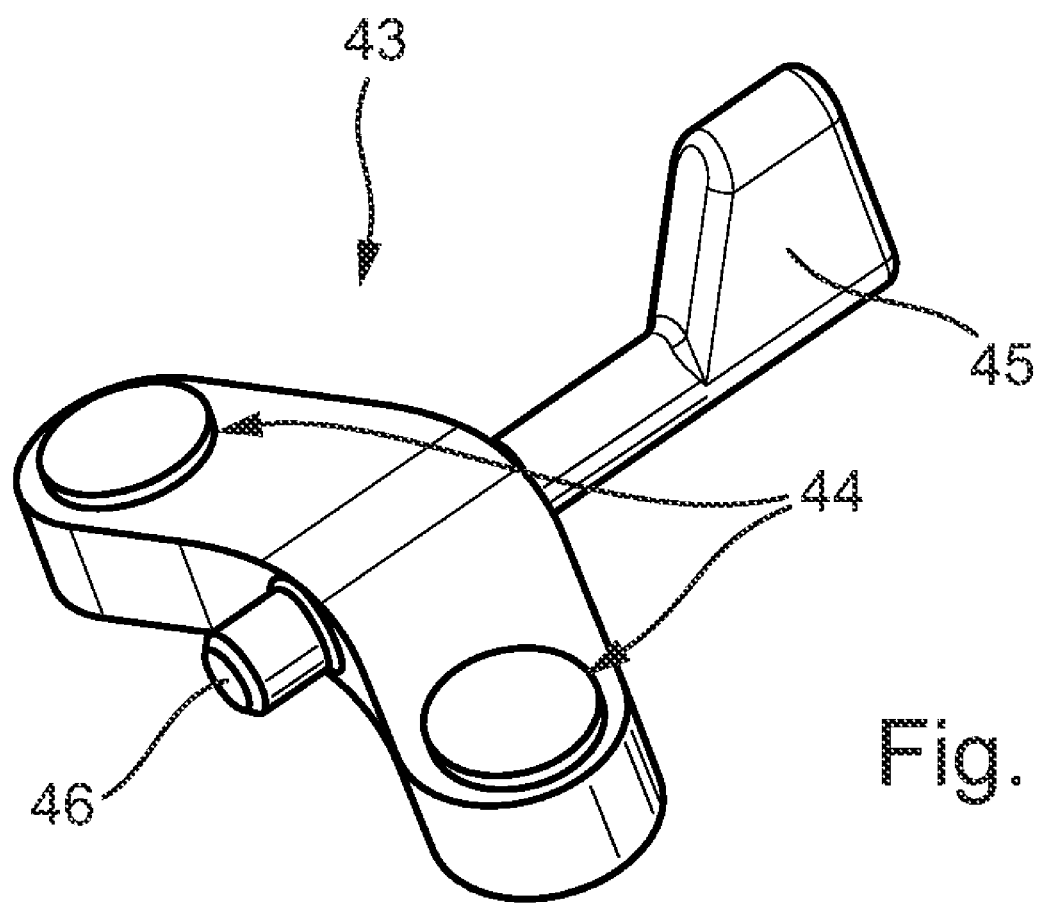

DOSING DEVICE FOR DOSING A FLUID INTO A RECEIVING CHANNEL OF A TEST ELEMENT FOR ANALYZING BODILY FLUIDS AND METHOD THEREOF

CROSS-REFERENCE TO RELATED APPLICATIONS

This application claims the benefit of priority under 35 U.S.C. §119 of European Patent Application No. 08 015 977.5, filed Sep. 10, 2008.

TECHNICAL FIELD

Embodiments of the present invention are directed generally to the field of medical analytics and, more particularly, to methods for analyzing bodily fluids, dosing devices for dosing fluids, and disposable cartridges for the dosing devices.

BACKGROUND

Systems for analyzing bodily fluid samples generally are classified as either "wet reagent analytical systems" or "dry reagent analytical systems."

Dry reagent analytical systems typically comprise test elements with integrated reagents. Such test elements are typically test strips, in which a fluid sample dissolves the reagents in the test strip and the reaction thereof results in a measurable change of a measured value. The measured value is measured on the test element using optical or electrochemical methods. Test systems of this type are cost-effective and simple to handle. However, a monitored and multistep reaction sequence is not possible using test strips and similar analysis elements. In particular, no control of a chronological sequence of individual reaction steps may be performed.

In contrast, multistep reaction sequences (test protocols) may be performed using wet reagent analytical systems. The high-performance devices allow a multistep reaction sequence, for example, as is necessary in immunochemical analyses. The reaction sequence frequently also comprises the separation of a bound phase and a free phase, a so-called bound/free separation. A plurality of test protocols for determining numerous analytes may be performed using wet reagent analytical systems. Though the test protocols can vary greatly, they all require complex handling with multiple reaction steps. Wet reagent analytical systems usually require technically complex, large-scale devices capable of moving individual elements. The devices used for this purpose are too large, costly, and complex to handle for many applications.

Analytical systems having controllable test elements unify the advantages of both types of analysis systems. They allow externally controlled liquid transport, i.e., a transport that is controlled using an element outside the test element. This external control may be based also on the application of pressure differentials or of change-of-force actions. An external control frequently is performed using centrifugal forces to act on a rotating test element. Nonetheless, these analytical systems are compact and simple to operate.

Controllable test elements typically have a housing comprising a dimensionally-stable plastic material, and at least one analytical-function channel enclosed by the housing. The analytical-function channel often comprises a sequence of multiple channel sections and expanded chambers lying between each section. The structures and dimensions of the analytical-function channel are achieved by profiling of the plastic parts, which are produced by injection-molding technologies or other known methods.

Analytical systems having controllable test elements allow the miniaturization of test protocols that previously required large laboratory systems. Therefore, relatively small quantities of a bodily fluid sample may be analyzed. The relatively small quantities typically are introduced via a dosing station into an analytical-function channel. The analytical-function channel also may be a sample analysis channel. Other analytical-function channels are used, for example, for receiving washing fluid or washing buffers are needed for performing the reaction sequences. Further fluids may be added such as, for example a reaction solution, a washing solution, or a dilution buffer.

Like the bodily fluid sample, also the liquids typically are supplied using a dosing station comprising a dosing pump, such as a piston pump, and a tube for injecting the fluid. The tube may be designated as a dosing needle. In addition, it is also possible to dose the fluids manually, for example, using a manual pipette or a syringe.

To dose small quantities of fluid using a dosing pump, fluid is supplied from a reservoir to a dosing chamber and then is discharged from the dosing chamber by the dosing needle. The volume of the reservoir is many times greater than that of the dosing chamber, so that the quantity of fluid stored in the reservoir is sufficient for a plurality of applications. However, this may also result in problems, because most quantities of fluid are subject to aging and may sit unused for an arbitrarily long time. Some of the fluids needed for the analysis may crystallize after long-term storage. The crystallized fluids then may clog the connection tubing and the dosing pump, requiring complex repairs. To prevent such clogging, the dosing stations must be cleaned and maintained frequently, and the tubing must be replaced regularly.

To avoid contamination, dosing devices known in the prior art comprise a replaceable dosing cartridge, which includes a reservoir, a dosing chamber having dosing piston, and a dosing needle. Systems of this type are known, for example, from US 2005/0035156 A1 and US 2007/0272710 A1.

For many reaction sequences, particularly those involving very small quantities of supplied fluid, the amount of fluid supplied must be very precise. A precision of a few tenths of a microliter is sometimes required. Thus, there remains a continued need for improved methods to precisely dose quantities of fluid being supplied to test elements in wet reagent analytical systems.

SUMMARY

Methods for precisely dosing a liquid into a receiving channel of a test element using a dosing device are disclosed. The test element is used for analyzing bodily fluids for analytes contained therein. Also disclosed are a dosing device for dosing a bodily fluid into the receiving channel of a test element, and a disposable cartridge for dosing a fluid into such a receiving channel.

In one embodiment, a method for dosing a fluid from a dosing device comprises acquiring a dosing device. The dosing device comprises a dosing chamber configured to hold the fluid, a dosing tube, a dosing tip of the dosing tube, a dosing element, a dosing control device, and a movement device. The dosing tube is in fluid connection to the dosing chamber. The a dosing element is movable to extend at least a part of the dosing element into the dosing chamber, thereby displacing a quantity of the fluid out of the dosing chamber. The part of the dosing element extending into the dosing chamber is then at least partially enclosed by the fluid in the dosing chamber. The dosing control device is configured to control a fluid flow from the dosing chamber through the dosing tube into a receiving channel of a test element. The movement device is configured to cause relative movement between the dosing tube and the test element.

The movement device is actuated to cause relative movement of the dosing tube and the test element from a rest position to an operating position. The rest position defines a first distance between the dosing tip and the receiving channel, and the operating position defines a second distance between the dosing tip and the receiving channel. The second distance is shorter than the first distance. Then, the dosing control device is actuated so as to discharge a defined quantity of the fluid from the dosing chamber, through the dosing tube, and into the receiving channel. The second distance, representing the operating position, is sufficiently small so that during the fluid discharge a fluid bridge is formed between the dosing tip and the receiving channel. Owing also to the sufficiently small second distance, at the end of the fluid discharge, at least a part of the quantity of fluid is transferred into the receiving channel by suction force. The movement of the dosing tube and the movement of the dosing element are coupled to one another.

In another embodiment, a dosing device comprises a dosing chamber, a dosing tube, a dosing control device, and a movement device. The dosing tube is in fluid connection to the dosing chamber and comprises a dosing tip. The dosing control device is configured to control a fluid flow from the dosing chamber through the dosing tube into a receiving channel of a test element. The movement device is configured to cause relative movement between the dosing tube and the test element from a rest position to an operating position. The rest position defines a first distance between the dosing tip and the receiving channel, and the operating position defines a second distance between the dosing tip and the receiving channel. The second distance is shorter than the first distance and is sufficiently small so that a quantity of fluid discharged from the dosing tip forms a fluid bridge between the dosing tip and the receiving channel, and, at the end of such a discharge, at least a part of the quantity of fluid transfers into the receiving channel through suction force.

In further embodiments, the dosing device may further comprise a dosing element comprising a portion that extends into the dosing chamber and is at least partially enclosed by the fluid in the dosing chamber. The dosing element is movable relative to the dosing chamber along a movement path from a starting position to an end position. When the dosing element is at the starting position, the portion of the dosing element that extends into the dosing chamber defines a first volume. When the dosing element is at the end position, the portion of the dosing element that extends into the dosing chamber defines a second volume greater than the first volume. The difference of the second volume and the first volume corresponds to a fluid volume displaced by the dosing element, the fluid volume corresponding to the quantity of fluid to be discharged.

In yet another embodiment, a disposable cartridge for dosing fluid into a receiving channel of a test element for the analysis of bodily fluids comprises a dosing module, a reservoir for fluid, and a connection tube for fluid connection of the reservoir and a dosing chamber of the dosing module. The dosing module comprises the dosing chamber and a dosing tube in fluid connection to the dosing chamber. The dosing tube is movable along a movement path comprising a rest position and an operating position. The rest position defines a first distance between a dosing tip of the dosing tube and the receiving channel, and the operating position defines a second distance between the dosing tip and the receiving channel. The first distance is greater than the second distance. The second distance is sufficiently small so that during a fluid discharge from the dosing tip a fluid bridge forms between the dosing tip and the receiving channel. At the end of such a fluid discharge, at least parts of the fluid are transported into the receiving channel through suction force.

These and other advantages and features of the invention disclosed herein, will be made more apparent from the description, drawings and claims that follow.

BRIEF DESCRIPTION OF THE DRAWINGS

Though the specification concludes with claims particularly pointing out and distinctly claiming the invention, it is believed that the present invention will be better understood from the following description taken in conjunction with the accompanying drawings, where like structure is indicated with like reference numerals and in which:

FIG. 9 shows a detail view of an embodiment of a rocker valve.

DETAILED DESCRIPTION

Figure 1A:
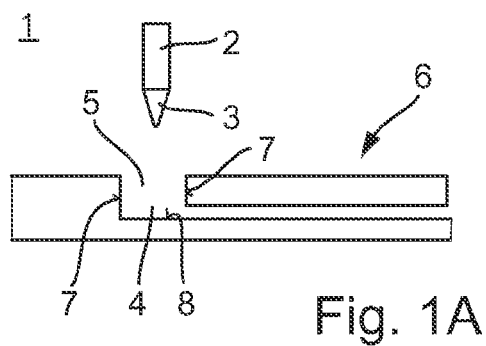
FIGS. 1A, 1B, 1C, and 1D schematically depict an approach of discharging a quantity of fluid from a dosing tube into a receiving channel of a test element.

Features and advantages of the invention will now be described with occasional reference to specific embodiments. However, the invention may be embodied in different forms and should not be construed as limited to the embodiments set forth herein. Rather, these embodiments are provided so that this disclosure will be thorough and complete and will fully convey the scope of the invention to those skilled in the art.

As used herein, the term "dosing" or any variant thereof means adding or discharging a desired measured (dosed) quantity of liquid with very high precision, further defined herein. As used herein, the term "fluid bridge" refers to a quantity of fluid that extends between a dosing tip of a dosing tube and a receiving channel of an analysis element. As used herein, the expression "end of the dosed fluid discharge" describes a state that is reached precisely when a dosing element is in its end position, as defined below. As used herein, the term "end position" refers to an endpoint of a movement path of a dosing element, in particular where the dosing element comes to a standstill.

A dosing system may comprise a dosing device and a test element. The system may have further components. It may also be part of an analysis system which, in addition to the dosing system having dosing device and test element, may comprise a measuring and analysis device, for example, and optionally an evaluation device and further apparatus and devices.

To dose a fluid into a receiving channel of a test element for the analysis of bodily fluids, a dosing device may be used. The fluid to be dosed may either be a sample fluid or also another fluid (liquid) needed for the analysis and the required reaction sequences, such as a washing buffer. The receiving channel is part of an analytical-function channel and may comprise a receiving opening, for example. In addition to the sample analysis channel, a washing channel or the like may also be used as the analytical-function channel.

A dosing device may include a dosing chamber and a dosing tube. The dosing tube is in fluid connection to the dosing chamber and is configured to transfer fluid from the dosing chamber into the receiving channel of the test element. The dosing device comprises a dosing tip, from which the fluid is discharged out of the dosing tube and into the test element. The dosing device comprises a dosing control device for the dosed control of the fluid flow from the dosing chamber through the dosing tube into the receiving channel. The dosing device comprises a movement device, by which a relative movement may be caused between the dosing tube and the test element.

The movement path of the relative movement includes a rest position and an operating position of the dosing tube relative to the receiving channel of the test element. The rest position defines a first distance between the dosing tip and the receiving channel, and the operating position defines a second distance between the dosing tip and the receiving channel, the second distance being shorter than the first distance. Thus, at the operating position, a dosing tip of the dosing tube is closer to the receiving channel than at the rest position. The movement device therefore may cause both a decrease of distance and an increase of distance between the dosing tube and the test element.

It is not relevant whether only one of the dosing tube and the test element is moved or whether both are moved relative to one another. Therefore, it is also possible to move the test element toward a stationary dosing tube until the operating position is reached. Though in some embodiments the test element is not moved toward or away from the dosing tube, but rather that the dosing tube approaches or is moved away from the test element, it will be understood that the relative movement between the dosing tube and the test element is not generally limited to movement of the dosing tube relative to a stationary test element.

The tip of the dosing tube is positioned proximate (sufficiently close) to the receiving channel of the test element in the operating position in such a manner that during the dosed discharge of the fluid from the dosing tube, a fluid bridge is formed between the dosing tip of the dosing tube and the receiving channel of the test element. At least parts of the quantity of fluid are transferred into the receiving channel by suction force at the end of the dosed fluid discharge.

At least at the end of the fluid discharge, the tip of the dosing tube and the receiving channel approach one another in such a manner that also the partial quantity of the fluid that last exits from the tip is drawn into the receiving channel in such a manner that no fluid remains on the outer side of the dosing tip. It follows that the entire quantity of fluid that has exited from the dosing tip will have been transferred into the dosing channel, without remaining elsewhere, such as hanging on the dosing tip, for example. The "last drop" is thus also drawn into the channel. In this manner, the quantity of fluid discharged into the channel is determined very precisely. Precisely the same quantity is discharged even after multiple sequential discharges of fluid, with at most negligible differences of discharged quantities among the multiple discharges.

Therefore, at the end of the fluid discharge the dosing tip is free of fluid on its outer side and/or tube mouth such that no fluid or only a negligible quantity of fluid adheres to the tip. In this manner, a dosing precision may be achieved which ensures a deviation of the dosed quantities of at most ±2.5 µL. The deviation is typically at most ±1.5 µL, in most cases at most ±0.5 µL.

Though the dosing device described above is capable of precise dosing of a liquid, the dosing device may further comprise a dosing element movable to extend at least a part of the dosing element into the dosing chamber. The extension of the dosing element into the dosing chamber displaces a quantity of fluid from the dosing chamber. The part of the dosing element extended into the dosing chamber is at least partially enclosed by the fluid in the dosing chamber.

Precise dosing of a liquid into a receiving channel of a test element for the analysis of bodily fluids may be performed using a dosing device according to any of the embodiments above or using a dosing system comprising the dosing device. In one embodiment, a method for precise dosing of a liquid using a dosing device from embodiments described above comprises the following steps:

In one step, the movement device is actuated so that the dosing tube is moved out of the rest position into the operating position. For this purpose, as described above, a relative movement is required between the dosing tube and test element. In another step, the dosing control device is actuated so that a defined quantity of fluid is discharged from the dosing chamber through the dosing tube into the receiving channel of the test element. This may be performed by moving the dosing element in the dosing chamber, for example. In one example embodiment, the dosing element may comprise a dosing piston.

As a result of the sequence of method steps, the dosing tip and the test element move into the operating position. During the dosed discharge a fluid bridge is formed. At the end of the dosed fluid discharge, parts of the fluid flow into the receiving channel driven by suction force. Also at the end of the fluid discharge, all parts of the fluid which have exited from the dosing tip have reached the receiving channel.

The movements of the dosing tube and the dosing element may be coupled to one another, in particular in such a manner that both movements can be driven by one common actuator or actuator element. The movements are coupled in such a manner that they can occur at least partially at the same time. They may occur synchronously, asynchronously, or offset in time with or without a chronological overlap. In some embodiments, the dosing tip may be positioned in the operating position during the dosed fluid discharge into the receiving channel of the test element. In some embodiments, the tip of the dosing tube is already in the operating position before fluid discharge begins. In any case, at the end of the discharge of the fluid to be dosed, or alternately before the end of the fluid discharge, the tip of the dosing tube must be located in the operating position so that a fluid bridge is formed between the dosing tip and the receiving channel and the "last drop" of the quantity of fluid to be dosed is drawn into the receiving channel.

The coupling of the movement of the dosing tube and the movement of the dosing element allows both components to be moved using only one actuator. In example embodiments, the coupling may be established by a lever configuration having one or more levers, by a rack and pinion configuration having a pinion, or by a spring configuration having one or more springs.

The order in which the method steps described above are performed is not critical. It is important only that the dosing tube be positioned in the operating position at least at the end of the fluid discharge, so that all of the fluid is transferred into the receiving channel.

In some embodiments, the dosing tip of the dosing tube may approach the receiving channel in the operating position in such a manner that the dosing tip is positioned within the receiving channel. In such a case, the dosing tube, or alternatively at least the dosing tip of the dosing tube, extends through the receiving opening into the receiving channel.

In the operating position of the dosing tube, the shortest distance between the dosing tip and a wall of the receiving channel opposite to the dosing tip in the movement direction is at most 1 mm, alternately at most 0.8 mm, alternately at most 0.7 mm, and alternately at most 0.5 mm. In a channel having essentially vertical side walls, the floor of the receiving channel is defined as the wall that is opposite in the movement direction. In funnel-shaped receiving channels, the floor of the receiving channel is the funnel wall. The shortest distance between the dosing tip and a wall and/or the floor is the length of a line from the dosing tip drawn perpendicular to the wall and/or the floor. Thus, the distance between the dosing tip and the edge of the receiving opening of the receiving channel hereinafter refers to the shortest distance.

Further embodiments of a dosing device may comprise a dosing element with a portion that extends at least partially into the dosing chamber. The volume of the dosing element is less than the volume of the dosing chamber and may be substantially less than the volume of the dosing chamber, for example, by a factor of 10. The part of the dosing element extending into the dosing chamber is enclosed at least partially by the fluid in the dosing chamber. In some embodiments, the part of the dosing element extending into the dosing chamber is completely enclosed by the fluid in the dosing chamber. The dosing element is movable on a movement path between a starting position and an end position.

When the dosing element is at the starting position, the portion of the dosing element that extends into the dosing chamber defines a first volume. When the dosing element is at the end position, the portion of the dosing element that extends into the dosing chamber defines a second volume. The second volume is greater than the first volume, and the difference of the second volume and the first volume corresponds to a fluid volume displaced by the dosing element. This fluid volume corresponds in turn to the quantity of fluid to be discharged through the dosing tip. As such, a smaller part of the dosing element is positioned in the chamber in the starting position, and a larger part of the dosing element extends into the chamber in the end position. The part of the dosing element additionally extending into the chamber between starting position and end position displaces the desired volume out of the dosing chamber.

As noted, the displaced volume corresponds to the quantity of fluid to be discharged. Because the dosing element does not contact the sidewalls of the chamber, as in a syringe, the displaced volume is independent of the dosing chamber. The displaced volume is a function of the shape of the dosing element only. Therefore, only the dosing element must be manufactured exactly and precisely. The dosing chamber itself, in contrast, does not require precision manufacturing. In this manner, the dosing chamber and the dosing device as a whole can be produced very cost-effectively.

In some embodiments, the dosing element may be implemented so that the dosing element have no contact with at least one side wall of the dosing chamber. With a cuboidal dosing element, four sides may be at least partially in contact with a fluid. With a cylindrical dosing piston or dosing element, the lateral surface is at least partially in contact with fluid. If there is no contact between the lateral surface and the inner walls of the dosing chamber, the dosing chamber does not have to be particularly precise in its dimensions. Thus, to discharge a precise quantity of fluid, it is sufficient for the volume of only the dosing element to be high-precision, alternately for at least the partial volume of the dosing element additionally extending into the dosing chamber between the starting position and the end position to be high-precision. It is therefore sufficient if only the dosing element is a precision part. The dosing device as a whole is thus very cost-effective, because high tolerances do not have to be maintained during the production of the dosing chamber.

The displaced quantity of fluid is discharged with the dosing element at the end position. At this moment, the partial quantity of the fluid which was last discharged from the dosing tip must also form a fluid bridge to the receiving channel and be drawn into the receiving channel by suction action, in such a manner that no residue remains hanging on the outer side of the dosing tip.

The precision fluid-dosing characteristics of the dosing devices described in the above embodiments can be achieved with a disposable cartridge also. As described above, the disposable cartridge may be a component of a dosing device, such as a dosing device described in the embodiments detailed above. The disposable cartridge comprises a dosing module, a reservoir for fluid, and a connection tube for fluid connection of the reservoir and a dosing chamber of the dosing module. The dosing module comprises the dosing chamber and a dosing tube in fluid connection to the dosing chamber. The dosing tube is movable along a movement path comprising a rest position and an operating position. The rest position defines a first distance between a dosing tip of the dosing tube and the receiving channel, and the operating position defines a second distance between the dosing tip and the receiving channel. The first distance is greater than the second distance. The second distance being sufficiently small so that during a fluid discharge from the dosing tip a fluid bridge forms between the dosing tip and the receiving channel. The fluid bridge also exists at the end of the dosed discharge. At least parts of the quantity of fluid reach the receiving channel through suction force at the end of the dosed fluid discharge. In this case, the last partial quantities of the fluid exiting from the dosing tip are suctioned completely into the receiving channel, so that no fluid, or only a negligible quantity of fluid, remains on the dosing tip of the disposable and thus replaceable cartridge. For very precise dosing, however, no fluid should be suctioned out of the interior of the dosing tip.

The disposable cartridge therefore comprises all parts and components which come into contact with the fluid to be dosed. When the reservoir of the cartridge is empty, when the limited-time storage life of the dosing fluid has expired, or when a defect such as sticking occurs on one of the fluid-conducting parts, the cartridge may be simply discarded. It is thus ensured that all fluid-conducting parts are replaced regularly. Costly and complex maintenance typically required of large dosing systems is avoided.

A specific, non-limiting embodiment of a method for dosing a fluid into a receiving channel of a movable test element or a rotatable test element is depicted in FIGS. 1A-1D. For clarity, only parts of a dosing device 1 are shown. In FIG. 1 only, a dosing tube 2 having a dosing tip 3 is shown. The dosing tube 2 is in fluid connection to a dosing chamber (not shown here), from which a fluid is discharged through the dosing tube 2 into a receiving channel 4 of a stationary test element 6. The receiving channel 4 has a receiving opening 5 on its top side. The test element 6 may be implemented as a disc, for example, similar to a compact disc for data or music, which disc may rotate horizontally around a rotational axis.

In a first step shown in FIG. 1A, a relative movement is performed between the dosing tube 2 and the test element 6. In the non-limiting example shown here, the test element 6 is fixed in its vertical position. The dosing tube 2 is moved downwardly in a direction toward the test element 6 until it reaches an operating position. In the operating position, the dosing tube 2 has approached the receiving channel 4 in such a manner that the dosing tip 3 extends through the receiving opening 5 into the receiving channel 4.

Figure 1B:
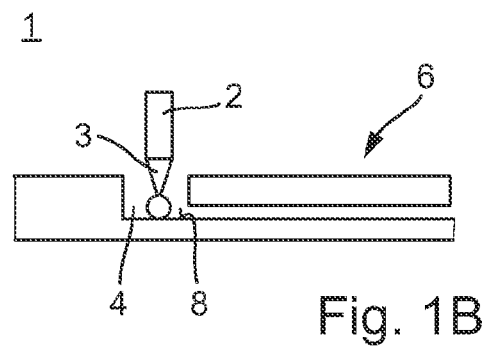

The discharge of a quantity of fluid now follows, shown in FIG. 1B as an example in the form of only one droplet. The dosing tip 3 still reaches the operating position before the end of the fluid discharge in any case. The dosing tip 3 may reach the operating position before the fluid discharge begins.

Figure 1C:
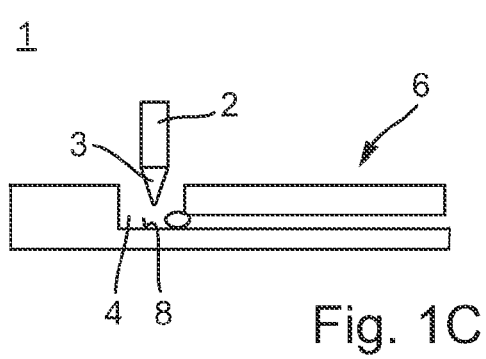
Figure 1D:
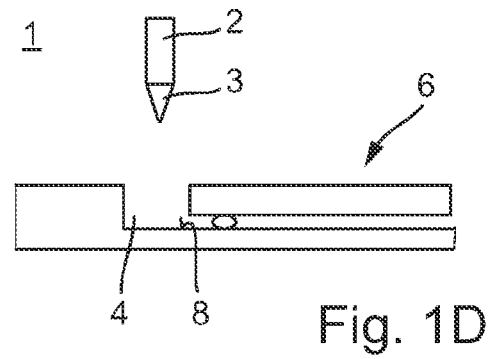

In the operating position, the dosing tip 3 has approached the walls 7 and the floor 8 of the receiving channel 4 in such a manner that a fluid bridge is formed to the floor 8 of the receiving channel 4. The fluid bridge also remains in existence at the end of the dosed discharge of the fluid. As illustrated in FIG. 1C, parts of the fluid reach the receiving channel 4 through suction force. As shown in FIG. 1D, the fluid droplet moves into the receiving channel 4 and is transported further therein by capillary action. The dosing tube 2 is moved upwardly, away from the test element 6, until it reaches its rest position. Because the suctioning of the fluid, including the last residue, occurs very rapidly (less than one second), the dosing tip 3 may be raised as quickly as one second, alternately 0.5 seconds after the end of the dosing procedure.

As may be inferred from the schematic images according to FIG. 1, very precise positioning of the dosing tip 3 is necessary. The dosing tip 3 approaches the test element 6 in such a manner that the smallest distance of its dosing tip 3 and the floor 8 of the receiving channel 4 is at most 1 mm. In this manner, it is possible to achieve dosing as precise as ±20%, for example, even with quantities of dosed fluid as small as, for example, 13 µL.

Figure 2:
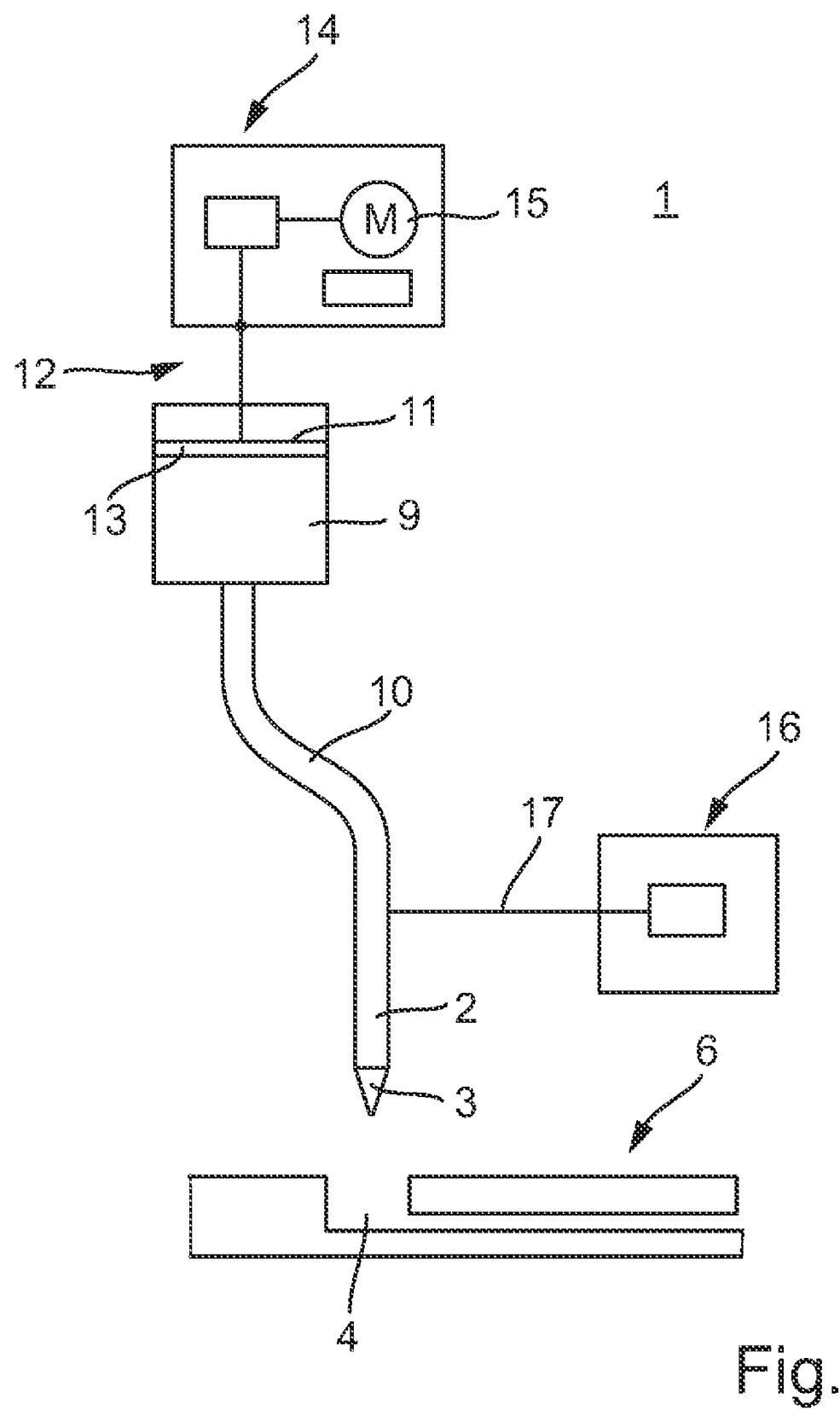
FIG. 2 shows a schematic sketch of an embodiment of a dosing device.

FIG. 2 shows a schematic view of an embodiment of a dosing device 1 and a test element 6, into the receiving channel 4 of which test element 6 a fluid may be discharged. In addition to the dosing tube 2 having the dosing tip 3, the dosing device 1 comprises a dosing chamber 9 in fluid connection with the dosing tube 2 via a flexible discharge tube 10. The dosing chamber 9 includes a dosing element 11 that is implemented as a piston 13. The piston 13, which is a component of a piston pump 12, extends into the dosing chamber 9 and is moved downwardly for the fluid discharge. The piston pump 12 is activated via a dosing control device 14, which comprises a motor 15 and a drive, for example, to drive the piston 13. The dosing control device 14 may comprise further components, for example an electronic controller, to implement targeted fluid discharge.

A movement device 16 comprises a drive for moving a lowering arm 17. The lowering arm 17 is connected to the dosing tube 2, so that a movement of the lowering arm 17 results in a movement of the dosing tube 2.

If the fluid to be dosed may crystallize, the tubes and pumps of the dosing device 1 must be cleaned and maintained regularly. Because all components are permanently installed and filled with the fluid to be dosed, cleaning and maintenance is very complex. For this reason, in alternate embodiments, the dosing devices may comprise a disposable cartridge.

Figure 3:
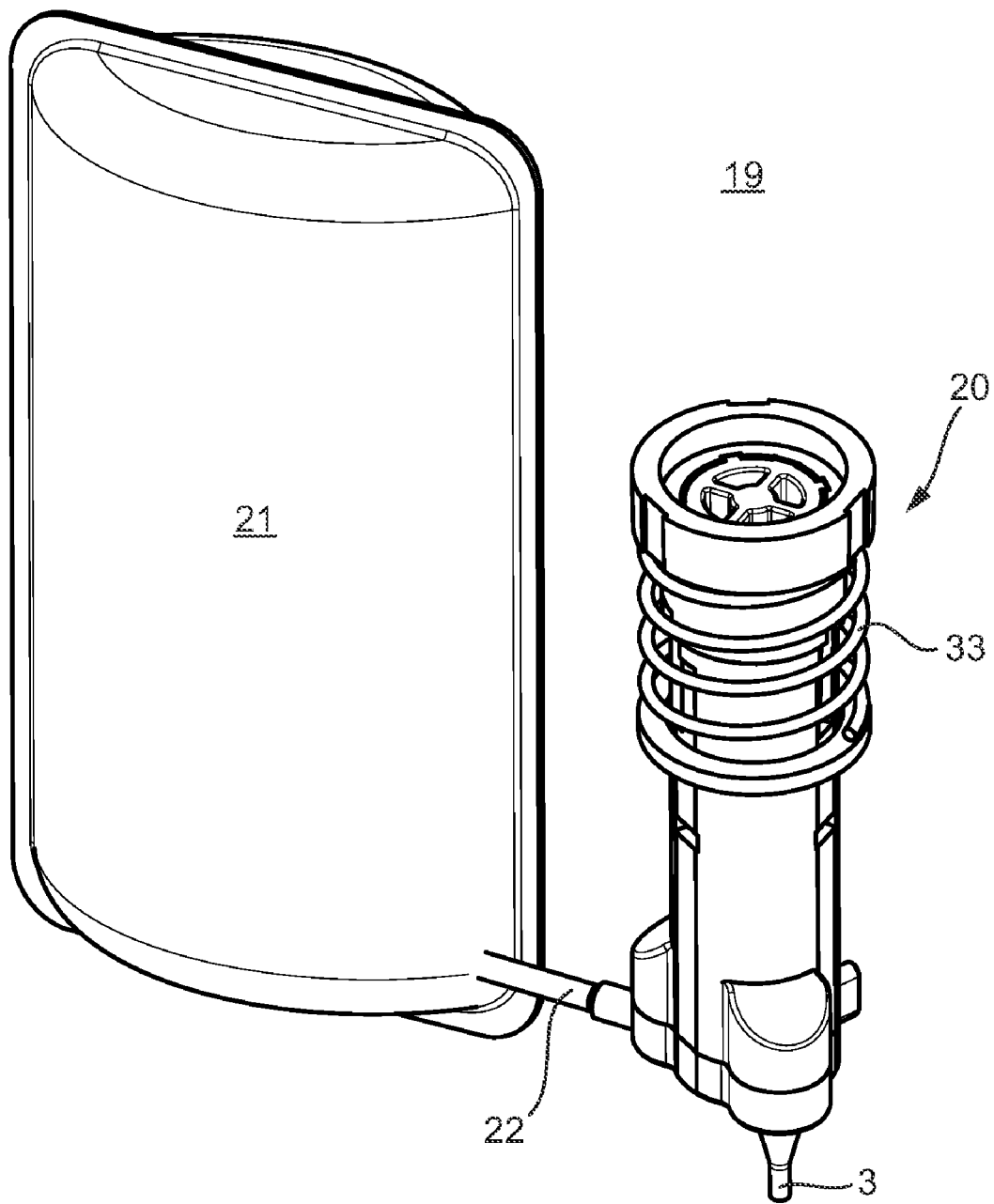
FIG. 3 shows an embodiment of a disposable cartridge having a dosing module and a reservoir.
Figure 4:
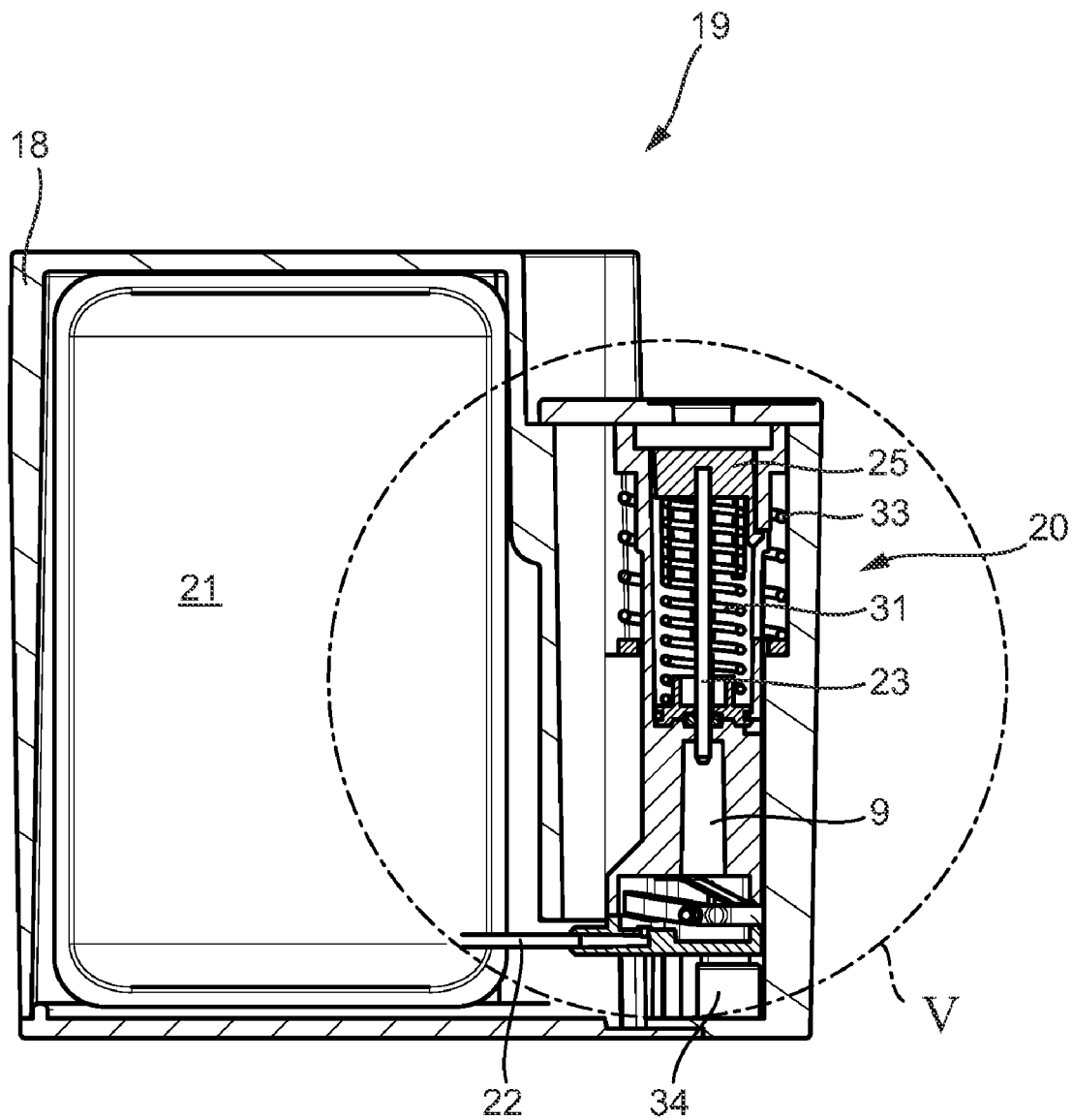
FIG. 4 shows a sectional illustration through the disposable cartridge depicted in FIG. 3.

A disposable cartridge 19 of a dosing device is shown in FIG. 3 (without housing 18) and FIG. 4 (with housing 18). The disposable cartridge 19 comprises a dosing module 20, a reservoir 21 for storing a larger quantity of the fluid to be dosed, and a connection tube 22 for the fluid connection between the reservoir 21 and the dosing module 20.

In some embodiments, the dosing module 20 of the disposable cartridge 19 may comprise the dosing chamber 9 and the dosing tube 2 having the dosing tip 3. In some embodiments, the dosing tube 2 and the dosing chamber 9, as components of the dosing module 20, may be fixed relative to one another in such a manner that they are movable jointly from the rest position into the operating position. Thus, a movement of the dosing tube 2 results in a movement of the dosing module 20 and the dosing chamber 9 also. In such an embodiment, the connection tube 22 may be implemented, for example, as flexible or bendable tubing. The movement of the dosing tube 2 is thus implemented by a movement of the dosing module 20 relative to the housing 18 of the disposable cartridge 19.

To integrate the disposable cartridge 19 in a dosing device 1, the disposable cartridge 19 is inserted into a receptacle (not shown) provided for this purpose. Because the complete dosing technology (including reservoir, dosing chamber, dosing element) is contained in the cartridge, only the (electrical) drive must be coupled to the cartridge via a mechanical interface, for example, via an actuator. The drives themselves are not components of the disposable cartridge 19, but rather remain in the dosing device 1 even when the disposable cartridge 19 is replaced. Because the dosing chamber 9 is connected fixed to the reservoir 21, a fluid coupling is avoided between the dosing module 20 and the reservoir 21.

Figure 5:
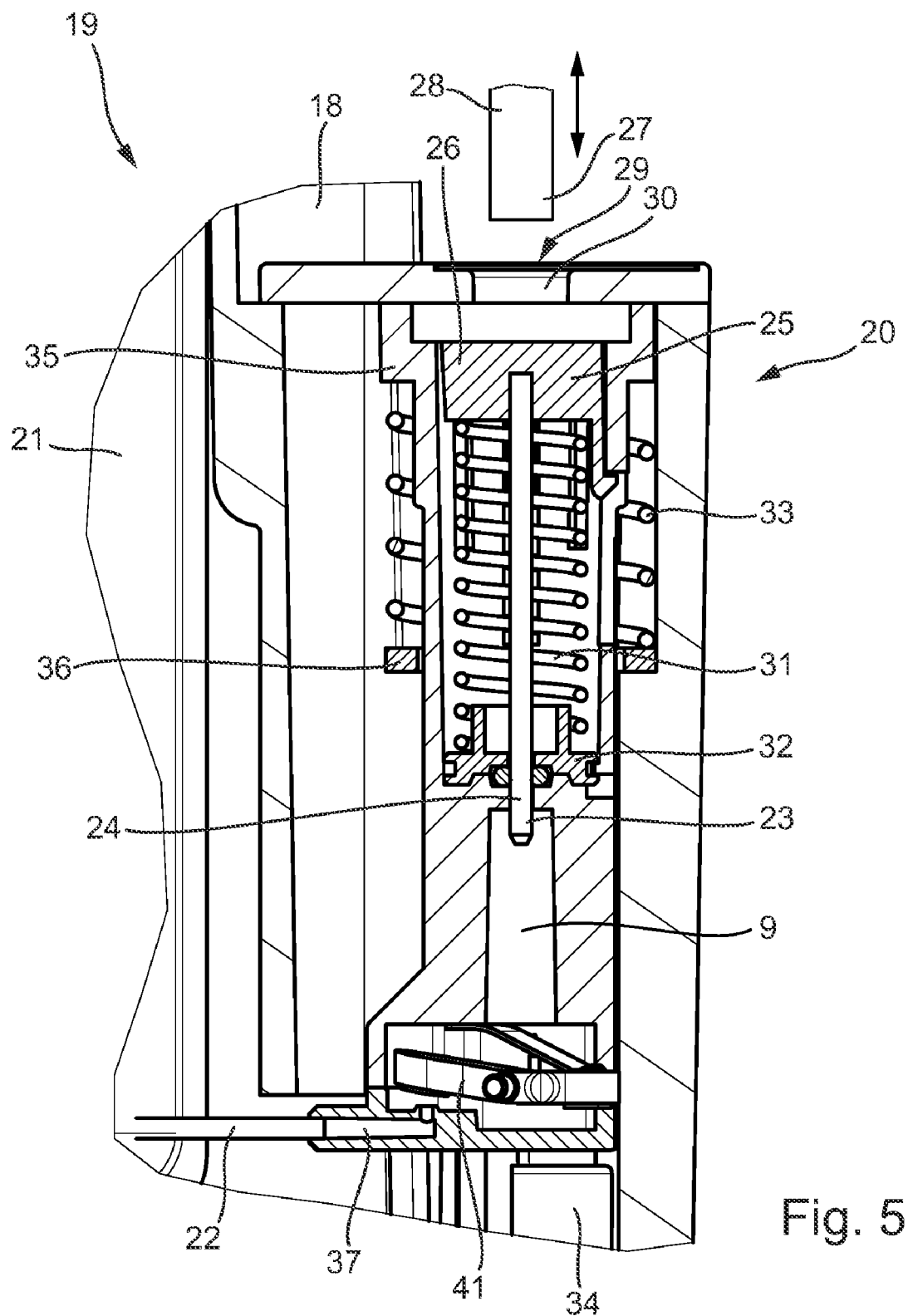
FIG. 5 shows a sectional illustration of a detail of the dosing module depicted in FIG. 3.

Referring to the embodiments shown in FIGS. 4 and 5, the dosing module 20 may also include a dosing element 23, such as a dosing piston 24, depicted here as a pin-like piston. The dosing element 23 partially extends into the dosing chamber 9. The dosing element 23 may be moved from a starting position (shown in FIG. 5), at which only a small part of the dosing element 23 extends into the dosing chamber 9, to an end position, at which a larger part of the dosing element 23 extends into the dosing chamber 9. This movement, in turn, displaces a desired quantity of fluid out of the dosing chamber 9. The part of the volume of the dosing element 23 that extends into the dosing chamber in the end position is significantly smaller than the volume of the dosing chamber. Thus, to ensure optimally precise discharge of a desired quantity of fluid, only the dosing piston 24 must be manufactured very precisely. Therefore, in some embodiments, the dosing piston 24 may be manufactured as a precision part produced from metal, alternatively from other materials such as, for example, plastics.

The dosing module 20 may comprise an actuator contact element 25 that may act on the dosing element 23. In some embodiments, a lowering of the actuator contact element 25 may cause a simultaneous lowering of the dosing element 23. The actuator contact element 25 may be implemented as a head part 26, shown in the example here as cylindrical, into which the upper end of the dosing piston 24 extends. The head part 26 and the dosing piston 24 are permanently connected to one another, for example, by gluing, welding, or connecting to one another in a similar manner.

The actuator contact element 25 may be actuated by an actuator 27 of the dosing device 1. The actuator 27 may be part of a movement device, of a dosing control device, or of a combined movement and dosing control device. For example, the actuator 27 may be a tappet 28 coupled to the actuator contact element 25 and capable of moving the actuator contact element 25 from top to bottom. In the embodiment shown in FIG. 5, a coupling is implemented by contacting (touching) the actuator 27 to the actuator contact element 25 and pressing the actuator 27 downwardly. To couple the tappet 28 on the head part 26, a film 29 is penetrated, the film 29 covering a housing opening 30 of the cartridge housing 18 above the head part 26. To penetrate the film 29 and move the actuator contact element 25, thereby effecting movement of the dosing element 23, the tappet 28 executes a linear (one-dimensional) movement. In some embodiments, the one-dimensional movement may be driven by a linear drive (not shown) of the dosing device 1.

In some embodiments, the dosing module 20 may be implemented in such a manner that the action of the one-dimensional movement of the actuator 27 on the actuator contact element 25 may cause both a movement of the dosing module 20 from the rest position to the operating position and a movement of the dosing element 23 from the starting position to the end position. Thereby, a single linear drive can effect both an approach of the dosing tip 3 to the receiving channel 4 and the desired fluid discharge. The dosing device 1 therefore may be constructed simply and cost-effectively. Because only one drive and only one actuator 27 are present, a dosing device of this type is also very robust.

In further embodiments the dosing element 23 and the dosing tube 2 may be coupled. Alternatively, the dosing element 23 may be coupled with the dosing module 20, the dosing module 20 comprising the dosing chamber 9 and the dosing tube 2 having the dosing tip 3. A coupling may comprise, for example, a lever configuration; a one-part or multipart linkage configuration; a clutch, such as a slip clutch; a configuration similar to a gearbox; or a spring configuration. Coupling arrangements such as these may be implemented to cause the movement of both the dosing module 20 and the dosing element 23 through a one-dimensional movement of the actuator 27. In non-limiting example embodiments, both movements may occur synchronously or asynchronously, at equal or different speeds, simultaneously or offset in time, or in a combination of these.

The dosing module 20 may include a dosing spring 31 that acts between the dosing chamber 9 and the actuator contact element 25. The spring force and spring action direction of the dosing spring 31 are dimensioned so that a pressure force exerted (downwardly) on the actuator contact element 25 first drives the movement of the dosing module 20 and then the movement of the dosing element 23. In some embodiments, the dosing element 23 may be driven only when or after the movement of the dosing module 20 has been stopped, such as be a stop 34.

The embodiment depicted in FIG. 5 shows that the dosing spring 31 is supported between the head part 26 and a spring support 32 of the dosing chamber 9, through which the dosing element 23 extends. The dosing spring 31 may be implemented as a coiled spring. As shown in the example embodiment, the dosing spring 31 may be compressed by the head part 26. In further embodiments, it is possible to implement the spring so that it is stretched out of its rest position by a downward movement of the head part 26. The dosing spring 31 shown in FIG. 5 encloses the dosing piston 24 in such a manner that it extends along the longitudinal axis of the coil of dosing spring 31.

In some embodiments, such as shown in FIG. 5, the dosing module 20 may comprise a lowering spring 33 that acts between the dosing chamber 9 and the stop 34. The stop 34 may be located on the housing 18 of the disposable cartridge 19. The action direction of the lowering spring 33 corresponds to the action direction of the dosing spring 31. In the embodiment shown in FIG. 5, the spring action direction is directed from top to bottom. The spring force of the lowering spring 33 is less than the spring force of the dosing spring 31. In this manner, a pressure force acting on the actuator contact element 25 first drives a downward movement of the dosing module 20 and subsequently drives a movement of the dosing piston 24. In some embodiments, the subsequent movement of the dosing piston 24 occurs only when or after the movement of the dosing module 20 has been stopped by the stop 34.

The dosing spring 31 and the lowering spring 33 may be selected in such a manner that the spring constant of the lowering spring 33 is less than the spring constant of the dosing spring 31. Alternatively, a stronger spring force of one of the springs relative to the other may be achieved, for example, by a bias tension of the particular spring, even if the springs have equal spring constants.

The dosing chamber 9 is connected spring-loaded to the housing 18 of the disposable cartridge 19 via the lowering spring 33. The lowering spring 33 is located between an upper collar 35 of the dosing module 20 and a lower, flange-type annular retention web 36. The lowering spring 33 is also compressed on movement of the actuator contact element 25.

In an example embodiment of a dosed discharge of fluid, a sequence of movements may progress as follows. First, the tappet 28 penetrates the film 29 and presses from above on the head part 26 of the actuator contact element 25. Thereby, the tappet 28 generates a pressure force that acts on the head part 26. Because the spring force of the lowering spring 33 is less than the spring force of the dosing spring 31, firstly the dosing module 20 is moved downwardly together with dosing chamber 9 until the dosing tip 3 reaches its operating position. The movement of the dosing module 20 from the rest position into the operating position occurs from top to bottom. In the operating position, the dosing module 20 abuts the stop 34. The stop 34 thus delimits the movement path of the dosing module 20 and thereby ensures a defined operating position of the dosing tip 3. Alternatively, the stop 34 may also be part of the dosing device 1 and thus independent of the disposable cartridge 19.

The force exerted by the tappet 28 now acts on the head part 26 and compresses the dosing spring 31, causing the dosing piston 24 to move into the dosing chamber 9. The volume displaced during this movement by the dosing piston 24 corresponds to the discharged quantity of fluid that reaches the receiving channel 4 of the test element 6 through the dosing tip 3.

After the desired quantity of fluid has been discharged from the dosing tip 3 into the receiving channel 4, the tappet 28 is moved upwardly. The dosing element 23, the dosing module 20, or both also are moved upwardly by the spring forces of the dosing spring 31 and the lowering spring 33 until the dosing element 23 returns to its starting position again and the dosing module 20 returns to its rest position. The movement of the dosing element 23 and the dosing module 20 are oriented according to the spring forces of the dosing spring 31, and the lowering spring 33. Their movements may occur in sequence, simultaneously, or offset in time. Because the spring forces of the dosing spring 31 and of the lowering spring 33 are oriented upwardly, it is sufficient for the tappet 28 to press against only the actuator contact element 25. Interlocking coupling is not necessary, because the tappet 28 must transmit forces only downwardly.

Figure 6:
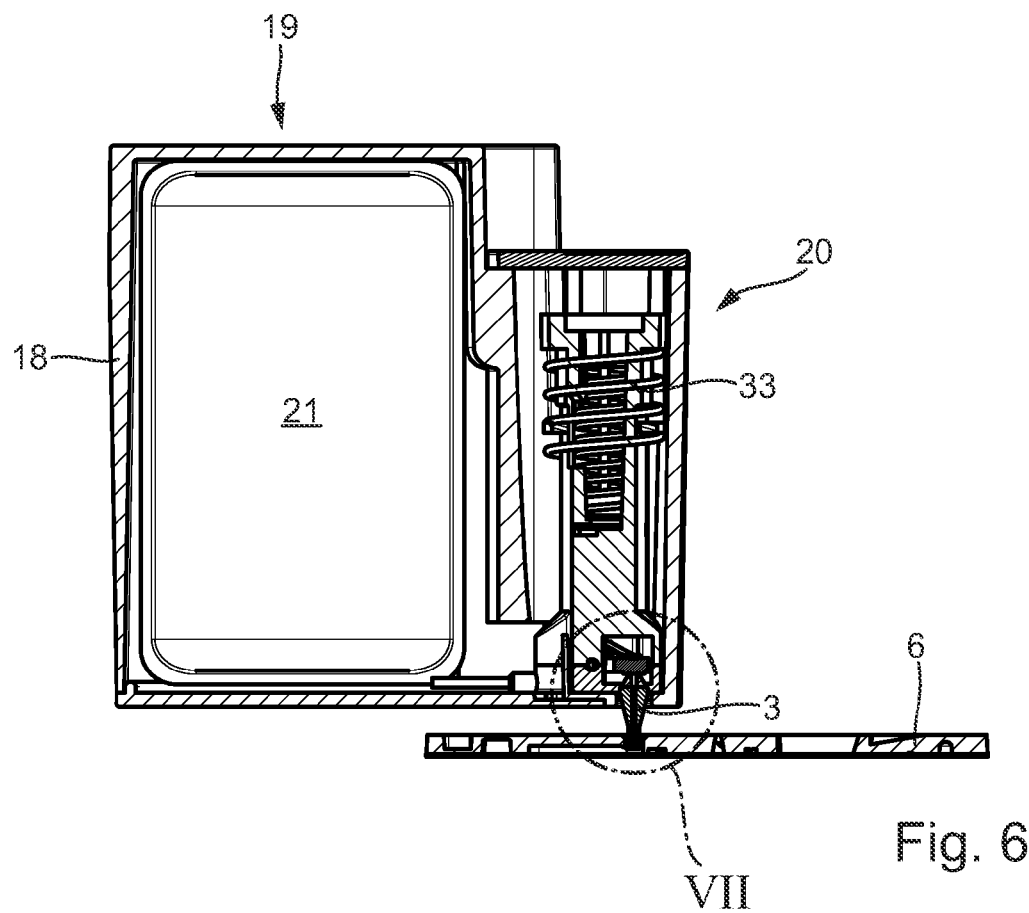
FIG. 6 shows a sectional illustration of an embodiment of a dosing device having a disposable cartridge and a test element.

FIG. 6 shows a further sectional illustration of an embodiment of disposable cartridge 19, with the dosing module 20 in its operating position. The dosing tip 3 has approached the corresponding receiving channel 4 of the test element 6 in such a manner that it extends through the receiving opening 5 into the receiving channel 4. The lowering spring 33 and the dosing spring 31 are completely compressed, so that the dosing piston 24 is located in its end position. The desired quantity of fluid has thus already flowed out of the dosing tip 3.

Figure 7:
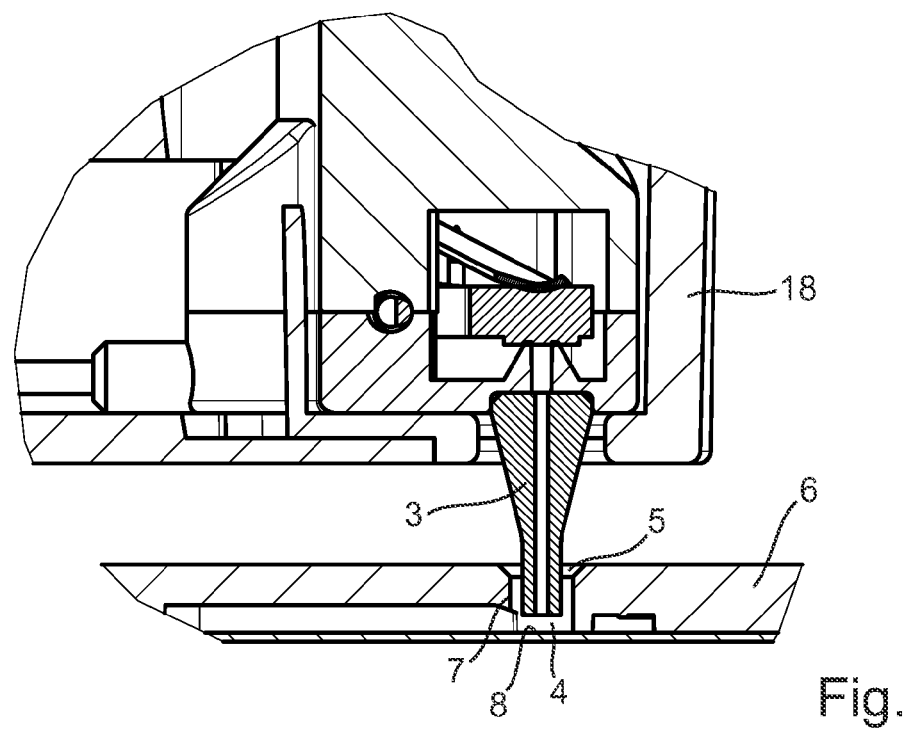
FIG. 7 shows a detail view of the embodiment shown in FIG. 6.

An example embodiment of a configuration of the dosing tip 3 in the receiving channel 4 is shown in detail in FIG. 7. It is clearly shown that no fluid residue remains hanging on the dosing tip 3. All of the quantity of fluid which has exited from the dosing tip 3 is drawn by the suction action into the receiving channel 4. The outer surface of the dosing tip 3 is free of fluid or has at most a negligible quantity of fluid remains adhered thereto. The suction action is caused by a combination of the cohesion force of the fluid, the adhesion force between fluid and floor 8 of the test element 6, and capillary forces of the receiving channel 4.

In some embodiments, the receiving channel 4 of the test element 6 may be hydrophilic and the dosing tip 3 of the dosing device 1 may be hydrophobic or be made hydrophobic. In such an embodiment, the suction action is increased and fluid transfer from the dosing tip 3 to the receiving channel 4 becomes more efficient.

In some embodiments, to ensure a reliable transfer of the fluid into the receiving channel 4, the distance between the dosing tip and the floor 8 of the test element 6 may be at most 1 mm. In the embodiment shown in FIG. 7, the dosing tip 3 has an internal diameter of 0.5 mm and an external diameter of 1.5 mm. As depicted, the distance from the dosing tip 3 to the floor 8 of the test element 6 is 0.8 mm to 0.6 mm. As depicted, the test element 6 is a total of 3 mm tall, accounting for an injection-molded layer made of plastic having a thickness of 2.7 mm and a self-adhesive floor film located underneath the plastic layer and having a thickness of 0.3 mm. Thus, as depicted, the dosing tip 3 extends approximately 1.9 mm to 2.1 mm into the receiving opening 5 of the test element.

In some embodiments, the dosing chamber 9 of the disposable cartridge 19 may comprise a fluid inlet 37, through which fluid may enter from the reservoir 21 and the connection tube 22 into the dosing chamber 9. The dosing chamber 9 of the disposable cartridge 19 may comprise a fluid outlet 38, through which a quantity of fluid may exit from the dosing chamber 9 into the dosing tube 2. The dosing chamber 9 of the disposable cartridge 19 may comprise both a fluid inlet 37 and a fluid outlet 38. The dosing chamber 9 of the disposable cartridge 19 may comprise an inlet valve 39 and an outlet valve 40 to control the fluid flows into and out of the dosing chamber 9. The inlet valve 39 may open and close the fluid inlet 37; the outlet valve 40 may close and open the fluid outlet 38.

Figure 8A:
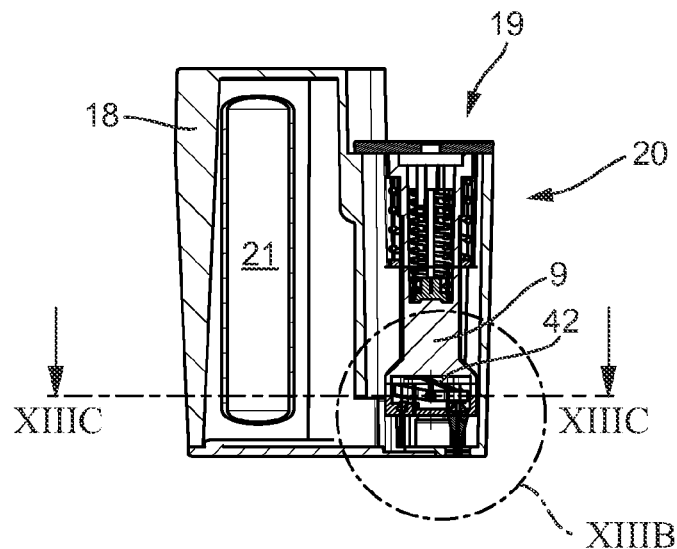
FIGS. 8A, 8B, and 8C show further section views of the disposable cartridge.
Figure 8B:
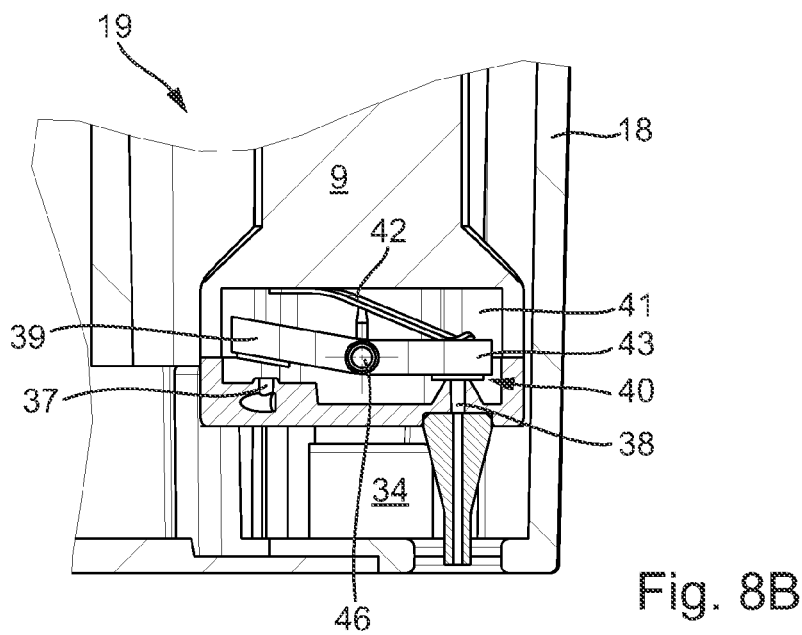
Figure 8C:
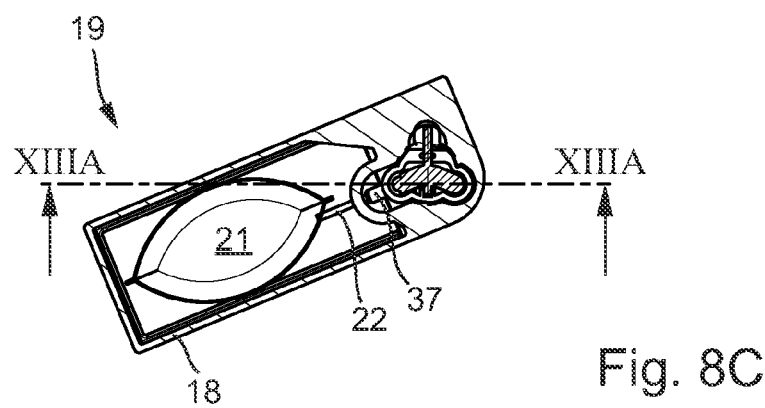

FIGS. 8A, 8B, and 8C show further section views through an example embodiment of the disposable cartridge 19. The inlet valve 39 and the outlet valve 40 are components of a valve unit, depicted in the figure in a non-limiting example as a rocker valve 41. In some embodiments, the rocker valve 41 may be implemented in such a manner that the inlet valve 39 and outlet valve 40 necessarily have different switching states. If one valve is open, the other valve is closed.

FIG. 9 shows the embodiment of the rocker valve 41 in detail. A rocker spring 42 acts on a valve rocker 43 of the rocker valve 41 in such a manner that the outlet valve 40 is closed in the rest position of the rocker valve 41 and thus no fluid may exit into the dosing tube 2. The valve spring 42 is may be implemented as a leaf spring; however, other springs are also possible. The valve spring 42 causes an automatic reset of the rocker valve 41 from the switched (open) state of the outlet valve 40 into the closed state. In order to ensure the best possible seal of the fluid inlet 37 and the fluid outlet 38, the valve rocker 43 has two round seal elements 44, which reliably close the inlet 37 and the outlet 38. The seal elements 44 may be extruded. In example embodiments, the seal elements 44 may comprise TPE (thermoplastic elastomer), for example. The seal elements 44 may be somewhat larger than the fluid inlet 37, the fluid outlet 38, or both the fluid inlet 37 and the fluid outlet 38.

A valve lever 45 may be molded onto the valve rocker 43, so that the rocker valve 41 may be actuated via a valve actuator (not shown). An electrical drive (not shown) may be provided for this purpose, so that the electrical drive moves the rocker valve 41 from its rest position into an open position of the fluid outlet 38. The valve actuator may be controlled by an external controller. The rocker valve 41 is thus externally controllable. It may be ensured both electronically and also mechanically that an actuation of the valve lever 45 is exclusively possible when the dosing tube 2, and thus the dosing module 20 also, are located in the operating position. Therefore, dosing of a fluid from the dosing chamber 9 is possible only when the dosing module 20 is in the operating position. If the rocker valve 41 is switched, the valve rocker 43 rotates approximately 10° (counterclockwise in FIG. 8B) around a valve shaft 46. The valve shaft 46 forms the rotational axis of the valve lever 45 and extends in elongation of the valve lever 45. Thereby, the switching of the rocker valve 41 closes the fluid inlet 37 and thus the reservoir 21, while simultaneously opening the fluid outlet 38 and thus the access to the dosing tip 3.

Means such as the external controller of the rocker valve 41 improve the operational reliability relative to a check valve, for example. This improvement is achieved by an increase of the (external) contact pressure forces, which thus can seal the valve more effectively. Furthermore, with a rocker valve 41 that is externally controlled and switched, the possibility exists of integrating a sensor unit for monitoring the valve setting in the dosing device 1, to recognize a maladjustment of the rocker valve 41. Thereby, contamination of the dosing device 1 or the test element 6 by a fluid contained in the reservoir 21, for example a washing buffer, can be prevented. Underdosing also can be prevented. The precise switching of the rocker valve 41 by the external controller can further increase dosing precision.

Persons skilled in the art will appreciate that the embodiments described herein may be subject to various improvements and/or modifications that may be apparent without departing from the spirit and scope of these embodiments.

What is claimed is:
1. A dosing system comprising:
   a test element having a receiving channel defined therein, the receiving channel having a receiving opening, and a floor and walls that transport a fluid through the receiving channel away from the receiving opening by capillary action; and
   a dosing device comprising:
      a dosing, chamber;
      a dosing tube in fluid connection to the dosing chamber, the dosing tube comprising a dosing tip;
      a dosing control device configured to control a fluid flow from the dosing chamber through the dosing tube into the receiving channel; and
      a movement device configured to cause relative movement between the dosing tube and the test element from a rest position to an operating position,
   such that:
      the rest position defines a first distance between the dosing tip and the floor of the receiving channel;
      the operating position defines a second distance between the dosing tip and the floor of the receiving channel;
      in the operating position the dosing tip extends through the receiving opening and into the receiving channel;

the second distance is sufficiently small so that a discharge of a quantity of the fluid from the dosing tip results in a fluid bridge between the dosing tip and the floor of the receiving channel; and at the end of the discharge, at least a part of the quantity of fluid is transferred into the receiving channel through a suction force caused by a combination of the cohesion force of the fluid, the adhesion force between the fluid and the floor of the receiving channel, and capillary forces of the receiving channel.

2. The dosing device of claim 1, wherein the dosing chamber and the dosing tube are components of a dosing module, the dosing chamber and the dosing tube being fixed in position relative to one another and being movable jointly from the rest position to the operating position.

3. The dosing device of claim 1, further comprising a dosing element, the dosing element comprising a portion that extends into the dosing chamber and is enclosed by the fluid in the dosing chamber, the dosing element being movable relative to the dosing chamber along a movement path from a starting position to an end position, such that when the dosing element is at the starting position the portion of the dosing element that extends into the dosing chamber defines a first volume, that when the dosing element is at the end position the portion of the dosing element that extends into the dosing chamber defines a second volume, that the second volume is greater than the first volume, and that a difference of the second volume and the first volume corresponds to a fluid volume displaced by the dosing element, the fluid volume corresponding to the quantity of fluid to be discharged.

4. The dosing device of claim 3, wherein the dosing chamber and the dosing tube are components of a dosing module, the dosing chamber and the dosing tube being fixed in position relative to one another and being movable jointly from the rest position to the operating position, and wherein the movement device is adapted to control movements of the dosing module and the dosing element in such a manner that the dosing module reaches the operating position before the dosing element reaches the end position.

5. The dosing device of claim 2, further comprising an actuator, wherein the dosing module further comprises an actuator contact element that acts on the dosing element when the actuator contact element is actuated by the actuator.

6. The dosing device of claim 5, wherein the dosing module is adapted such that a one-dimensional movement of the actuator acting on the actuator contact element actuates movement of the dosing module from the rest position to the operating position and movement of the dosing element from the starting position to the end position.

7. The dosing device of claim 6, characterized in that the dosing module comprises a dosing spring, the dosing spring acting between the dosing chamber and the actuator contact element and having a spring force and a spring action direction dimensioned so that a pressure force exerted on the actuator contact element first drives the movement of the dosing module and then drives the movement of the dosing element.

8. The dosing device of claim 7, further comprising a lowering spring, the lowering spring acting between the dosing chamber and a stop configured to stop movement of the dosing module effected by the dosing spring, the lowering spring having an action direction and a spring force, the action direction of the lowering spring corresponding to the action direction of the dosing spring, the spring force of the lowering spring being less than the spring force of the dosing spring.

9. The dosing device of claim 2, further comprising a disposable cartridge, the disposable cartridge comprising the dosing module, a reservoir for fluid, and a connection tube for fluid connection between the reservoir and the dosing chamber.

10. The dosing device of claim 9, wherein the dosing chamber comprises a fluid inlet, through which fluid can enter from the reservoir into the dosing chamber, and a fluid outlet, through which fluid can exit from the dosing chamber into the dosing tube.

11. The dosing device of claim 10, wherein the dosing chamber further comprises an inlet valve for closing and opening the fluid inlet, an outlet valve for closing and opening the fluid outlet, or both.

12. The dosing device of claim 11, further comprising a valve unit comprising the inlet valve and the outlet valve, the valve unit being configured such that the inlet valve and the outlet valve necessarily have different switching states.

* * * * *

UNITED STATES PATENT AND TRADEMARK OFFICE
CERTIFICATE OF CORRECTION

| | | |
|---|---|---|
| PATENT NO. | : 8,043,582 B2 | Page 1 of 1 |
| APPLICATION NO. | : 12/556216 | |
| DATED | : October 25, 2011 | |
| INVENTOR(S) | : Andreas Bauer et al. | |

It is certified that error appears in the above-identified patent and that said Letters Patent is hereby corrected as shown below:

Title Page

(30) Foreign Application Priority Data, "08015977" should read --08015977.5--; and

(14) Detailed Description, Column 14, Claim 1, Line 52, "a dosing, chamber;" should read --a dosing chamber;--

Signed and Sealed this
Tenth Day of April, 2012

David J. Kappos
*Director of the United States Patent and Trademark Office*